(12) United States Patent
Schossau (10) Patent No.: US 7,374,566 B1
(45) Date of Patent: May 20, 2008

(54) SURGICAL KNIVES FOR LARGE, SELF-SEALING CORNEAL INCISIONS COUPLED TO A UNIVERSAL INTRAOCULAR LENS (IOL) INJECTOR

(76) Inventor: Tom M. Schossau, 192 Garth Rd. #6-0, Scarsdale, NY (US) 10583

( * ) Notice: Subject to any disclaimer, the term of this patent is extended or adjusted under 35 U.S.C. 154(b) by 922 days.

(21) Appl. No.: 10/268,307

(22) Filed: Oct. 10, 2002

(51) Int. Cl.
*A61F 9/007* (2006.01)
(52) U.S. Cl. ..................................... 606/167; 606/107
(58) Field of Classification Search ................ 606/107, 606/166, 167, 160, 161, 169; 30/136, 148, 30/149, 299, 323, 327, 328, 346.55–346.57
See application file for complete search history.

(56) References Cited

U.S. PATENT DOCUMENTS

| 2,647,310 | A | * | 8/1953 | Yolles | 30/149 |
| 4,225,854 | A | * | 9/1980 | Davis et al. | 341/134 |
| 4,286,384 | A | * | 9/1981 | Kotchy | 30/287 |
| 4,787,146 | A | * | 11/1988 | Gaskins | 30/299 |
| 5,122,152 | A | * | 6/1992 | Mull | 606/170 |
| 5,713,915 | A | * | 2/1998 | Van Heugten et al. | 606/167 |
| 5,797,937 | A | * | 8/1998 | Ichikawa et al. | 606/167 |
| 5,896,667 | A | * | 4/1999 | Hawkins | 30/294 |
| 6,503,262 | B1 | * | 1/2003 | Edens | 606/167 |
| 6,547,802 | B1 | * | 4/2003 | Nallakrishnan et al. | 606/166 |
| 6,554,840 | B2 | * | 4/2003 | Matsutani et al. | 606/107 |
| 6,908,476 | B2 | * | 6/2005 | Jud et al. | 606/205 |

* cited by examiner

*Primary Examiner*—Todd E. Manahan
*Assistant Examiner*—Elizabeth Houston
(74) *Attorney, Agent, or Firm*—Robert Nathans (57) ABSTRACT

A lens injector includes a thin sheet-like lens glide member, mounted upon a tapered knife, that maintains a wedge-shaped opening in the cornea upon withdrawal of the knife. The lens is thereafter advanced under the cornea by a plunger in the injector that maintains the lens in place as the injector device is removed. A multiple point blade knife may simultaneously make a set of several small, connected incisions. The fact that each blade has only a limited depth means that the resulting wide incision can be created without the need to penetrate deeply into the cornea, as would be necessary with a single-point blade of the desired width. This is especially beneficial for creating Z-shaped incisions, which become self-sealing when internal pressure pushes the inner layer against the outer layer. This shortens the process significantly, which then results in less trauma to the eye and streamlines the entire procedure.

29 Claims, 7 Drawing Sheets

SURGICAL KNIVES FOR LARGE, SELF-SEALING CORNEAL INCISIONS COUPLED TO A UNIVERSAL INTRAOCULAR LENS (IOL) INJECTOR

BACKGROUND OF THE INVENTION

Figure 1:
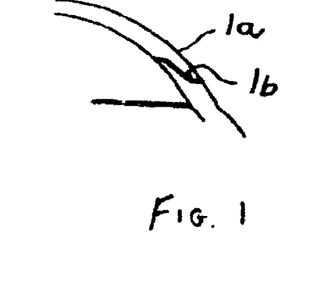
FIG. 1 illustrates a prior art Z-stroke incision.

Implantation of lenses (Phakic intraocular lenses, or PIOLs) inside normal or phakic eyes to correct vision, while retaining the ability to focus up close, has been gaining favor and popularity. Recent improvements in the quality of the IOL and the discovery by many patients that they do not qualify for laser surgery on the cornea [such as LASIK (laser-assisted in situ keratomileusis), LASEK (laser epithelial keratomileusis), or PRK (Photo Refractive Keratectomy)] mean that Phakic IOLs are increasingly in demand. In addition, it is becoming apparent that individuals qualified for both laser surgery and IOL implantation who require higher powers of correction are generally more satisfied with the Phakic IOL procedure, because it results in better quality of vision. One drawback to the Phakic IOL solution is the need for sutures to close a large incision in the cornea after implantation of a (nonfoldable) lens. Use of sutures is time-consuming and usually causes unavoidable astigmatism or blurry vision. It has been proven that a Z-stroke (Langerman) or multi-planar incision 1b in the cornea 1a (FIG. 1) creates an incision "flap" that, because of the eye's internal pressure, is self-sealing, eliminating the need for sutures. With currently available knife blades, incisions of this kind that are as much as 5-6 mm wide are successfully self-sealing (Koch, Shelton). However, current Phakic IOL implantation procedures necessitate larger 7-mm incisions. Using currently available instruments to create these larger incisions requires an inefficient process of making multiple strokes, and using multiple instruments, and the results have not yet been proven to be self-sealing.

At this time there are very few instruments designed to handle the larger-sized, (nonfoldable) Phakic IOLs, and no type of a device for injecting this type of lens or a variety of lens is available. Therefore, some new type of instrument is needed to create a large incision that is self-sealing, and then to place this lens into the eye more efficiently.

It has been proven that a Z-stroke (Langerman) or multi-planar incision 1b in the cornea 1a (FIG. 1) creates an incision "flap" that, because of the eye's internal pressure, is self-sealing, eliminating the need for sutures. With currently available knife blades, incisions of this kind that are as much as 5-6 mm wide are successfully self-sealing, Koch, Paul S., M.D. Converting to Phacoemulsification. Slack Inc., Thorofare, N.J., 1992, pp 3-29.

However, current Phakic IOL implantation procedures necessitate larger 7-mm incisions.

Figure 2:
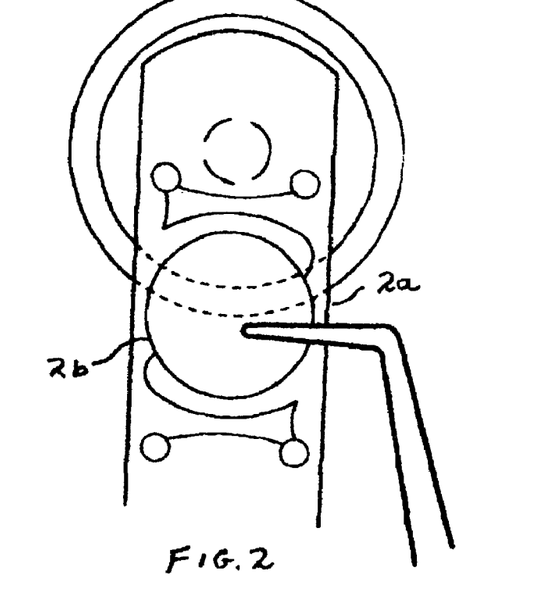
FIG. 2 illustrates prior art aspects of prior art surgical procedures for phakic IOL surgery.

Current Surgical Procedure for Phakic IOLs (FIG. 2): About a week preoperatively, a (Nd:YAG) Laser Peripheral Iridotomy (LPI) is usually performed to make a small hole in the iris to prevent acute glaucoma, a sudden rise in pressure, when this type of IOL is inserted. Just prior to surgery, pilocarpine (4%) drops are instilled to constrict the pupil, and anesthesia is then given. Surgery begins by making a side-port incision into the cornea and injecting viscoelastic fluid into the anterior chamber to make the eye firmer, which aids in making better incisions. The surgeon then makes a 7.0-mm incision into the cornea, usually using two or more instruments such as a forceps, microsharp, keratome, and possibly scissors. Usually a lens glide 2a is manually placed inside the eye with forceps to serve as a guide for positioning the IOL 2b and to protect the natural lens and iris during placement (FIG. 2). The surgeon then uses forceps in one hand to grasp and lift the corneal flap and to give counter-traction, while manipulating another forceps in the other hand to insert the IOL into the anterior chamber. After removing the lens glide, the surgeon uses forceps to position the IOL under the corneal shelf and into the proper angle between the iris and the cornea. Finally, the anterior chamber is irrigated to remove the viscoelastic material, and sutures are placed to close the corneal incision. This, procedure depends upon the skill of the surgeon, but usually requires about 20 minutes, 20 percent of which may be spent in placing sutures to close that incision. The fact that astigmatism results from the use of sutures is nearly unavoidable (Koch). The source for this current procedure was www.oii-iol.com.

Wishinsky (U.S. Pat. No. 5,217,476) and Lager (U.S. Pat. No. 5,217,477) propose dual widths of a surgical knife to make two precise and separate incisions for the phaco tip (3.2 mm) to remove the cataract and then for the IOL (5.2 mm) to be inserted. In a similar concept but for different purposes, a less tapered blade with a steeply tapered and very short point form two widths (FIG. 4) but for the purpose of allowing the surgeon to make the single, much larger IOL incision (6-7 mm) more easily and may optionally make the small side port incision (1 mm) with just the tip.

Praeger (U.S. Pat. No. 4,676,792) noted that a ridged lens glide provides better control than a flat lens glide and allows better exposure to manipulate the lens than an envelope-type lens glide. A semi-rigid lens glide with a tip that is flat and flexible, and a base that has a rigid bottom and similar ridged sidewalls allows for similar exposure but for greater maneuverability of the IOL once inside the eye. This semi-rigid lens glide also forms a wedge to efficiently open the incision for the insertion of the IOL.

For the purpose of "wicking" out fluid from the eye to lower the pressure in glaucoma patients, Simon (U.S. Pat. Nos. 5,651,782 and 5,676,679) proposes a surgical knife with a wedged blade that makes an incision and inserts an artificial meshwork underneath the blade from behind the wedge. In a similar manner, a knife blade is wedge-shaped to open the incision on top to co-insert another instrument, the IOL Injector.

Rhein Medical, Inc. (US Patent RE37,304) describes a beveled blade of specified different taper on both faces where both sides or shoulders are slightly thicker than the center for the stated purpose of making an incision but not of any sufficient thickness or description to form a wedge for the intended purpose of co-inserting another device. The blades in this design may have different taper in the bevel to form a wedge, and/or may be thicker in the sides or shoulders for efficiency. However, these features are not essential to form a basic mechanical wedge involved in the present invention that functions to open the incision upward, allowing the insertion of the tip of the lens glide that lies in a "scooped-out valley" on the top of the blade and behind this wedge.

BRIEF SUMMARY OF PREFERRED EMBODIMENTS OF THE INVENTION

Figure 11:
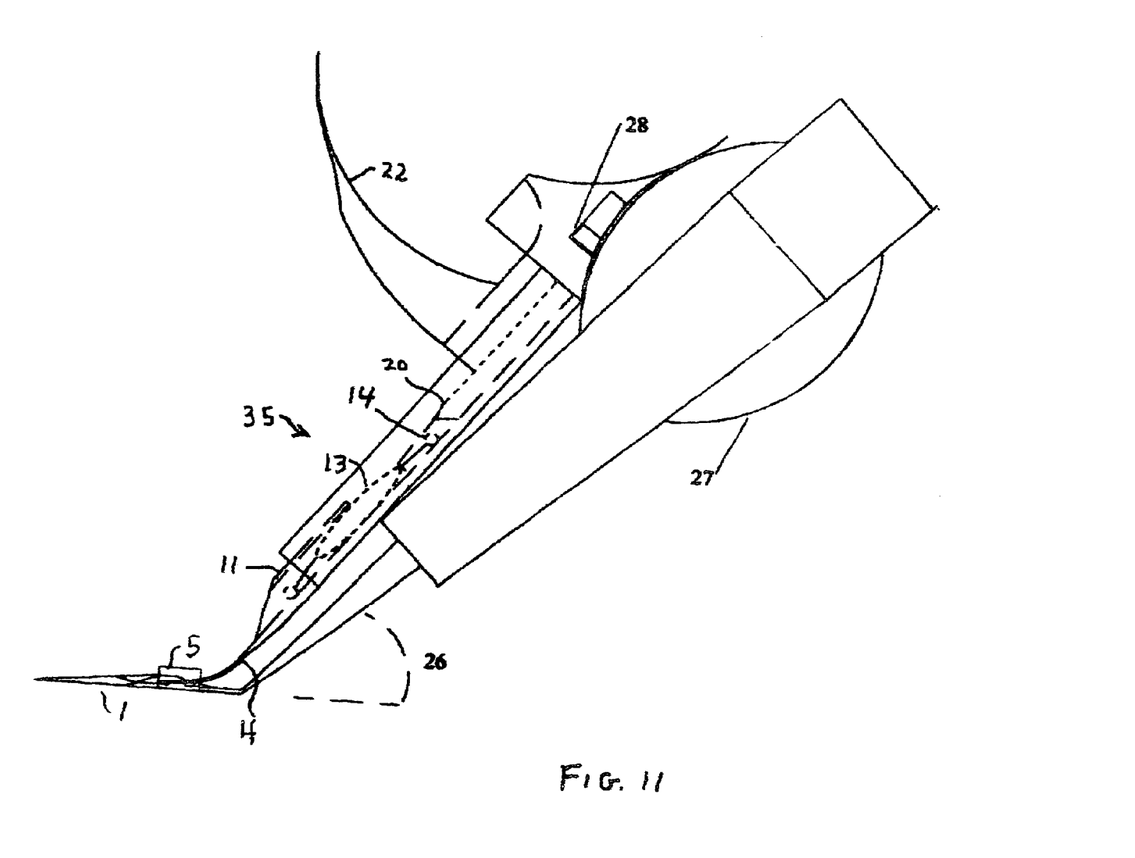
FIG. 11 shows the complete IOL Injection System, with the keratome (and its handle) coupled to the IOL Injector.

As shown in FIG. 11, the three-component intra-ocular lens (IOL) Injector system includes (a) a keratome wedge shaped knife 1 for creating the self-sealing incision in the cornea of the eye, (b) a lens glide member 10 "piggy-backed" on the knife, which glide member maintains a wedge-shaped opening in the cornea, and (c) an inserter member or plunger 20 that pushes the lens into the eye, the latter two components being part of the injector device 35. The intra-ocular lens injector device 35 attaches directly to the wedge-shaped keratome knife blade so that, as soon as the incision is made in the cornea, the surgeon can replace the blade with the injector device in one motion.

The surgeon places the lens upon a protective plastic sheet of the lens glide member that has side walls on it; these side walls 11 act as rails and guide the lens 13 unimpeded through the incision when the surgeon pushes on a plunger or inserter member 20 within the injector device. Once the lens is completely inside the eye, the surgeon withdraws the injector device, which leaves the lens in position and allows the flaps of the incision to seal the eye without the need for sutures. More specifically, the lens glide member comprises a lens glide 10 attached to a receptacle for the IOL 13. After the wedge-shaped knife 1 is fully inserted through the cornea into the eye, the tip of the "piggy-backed" lens glide is automatically positioned just inside the incision and behind the knife wedge. At this point, the surgeon pushes the lens glide slightly forward to wedge it into the eye. While holding the device so that the tip of the lens glide remains wedged inside the incision, the surgeon then removes the keratome blade 1, inserts the lens glide member 10 fully into the eye, and pushes an inserter or plunger 20 against the lens optic 13 or haptic 14 to seat the lens inside the eye. Like the magician snatching a tablecloth out from under dinner plates, the surgeon thereafter retracts the lens glide member while the plunger holds the lens in place inside the eye. After withdrawing the plunger, the surgeon inflates the eye through the side-port incision and checks the larger IOL incision for leakage.

The blade 1 is wedge-shaped and has a "scooped-out" valley in the heel of the blade face, to allow the tip of the lens glide to also be inserted into the eye along with the blade. Stops 5 on the blades provide better control and safety, preventing accidental movement by the patient or surgeon that may cause harm. These stops also serve as a channel on the face of the blade to contain the lens glide. The lens glide member, in contrast with the Praeger patent, has wedge-shaped sidewalls 11 on top to wedge open the incision from above, and to channel or guide the lens 13 into the eye during insertion. This lens glide member is shaped like a boat underneath to efficiently provide room for the lens, while providing structural support and helping to open the incision from below. The lens glide member is also ergonomically designed to provide greater control and comfort for either a right- or left-handed surgeon, and for either a one- or two-handed procedure. A ball-like collar 27 on the keratome handle, much like designs currently used for writing pens, also provides for greater control by and comfort of the surgeon.

The IOL injector system employs novel keratome knives having multiple blade tips that create a wide incision by simultaneously making a set of several small incisions that are connected together in one stroke. The fact that each blade tip has only a limited depth to cut a flap means the resulting wide incision can be created without the need to penetrate deeply into the cornea, as would be necessary with a single-point blade of the desired width. This is especially beneficial for creating Z-shaped incisions, which become self-sealing when internal pressure pushes the inner layer against the outer layer. Because an incision made orthogonal to the tangential plane of the cornea is known to leak (Koch), these blades and incisions are designed to avoid this maneuver. The capability to make multiple such Z-shaped incisions in a single stroke is a major advance that shortens the process significantly, which in term results in less trauma to the eye and streamlines the entire procedure.

BRIEF DESCRIPTION OF THE DRAWINGS

FIGS. 4-6 and 12 depict views from the front (-F), top (-T) and side (-S) of the device. The two dotted concentric circles shown in these figures represent the cross-section of a cornea 12.0 mm in diameter with a thickness of 1.0 mm at its base (level of the limbus). The view of the cornea appears much like slicing a tennis ball through the center. Similarly, FIG. 6-S (side view) depicts one quarter of a cornea, between the level of the iris plane and the cornea at the anterior apex, like taking one quarter of a tennis ball;

More specifically.

DETAILED DESCRIPTION OF PREFERRED EMBODIMENTS OF THE INVENTION

FIG. 11 shows the complete IOL Injector System, with the IOL Injector coupled to the keratome. The neck 26 of the keratome 1 is bent at its usual angle (approximately 45 degrees). The top of the ball-like collar 27 on the handle of the keratome has a small, 2-mm pin 28 to further stabilize the IOL Injector and to limit the forward movement of the lens glide into the eye for safety.

The keratome consists of a blade 1 and a handle. The blades are intended to be made of disposable, surgical stainless steel, but may be made of other hard, diamond-like material. The keratome handle is made from a rigid, inert, polymer-like substance. This handle has an adjustable, rubbery, ball-like collar 27 similar to common designs for writing pens to stabilize the IOL Injector and to provide better control and comfort for the surgeon.

Figure 4F:
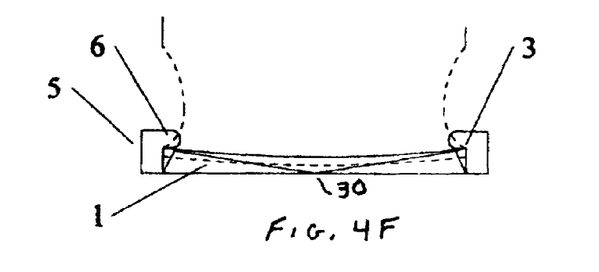
FIG. 4 is a wedged keratome 7.0 mm wide with a tapered point for better initial penetration. The blade can optionally serve as a microsharp to make side port incisions. This blade is less tapered than other "standard" keratomes (top view) to create a wider flap to better seal larger incisions.
Figure 4S:
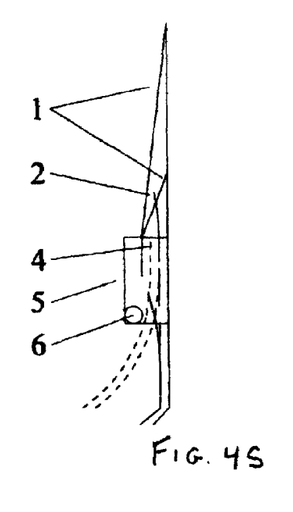
Figure 4T:
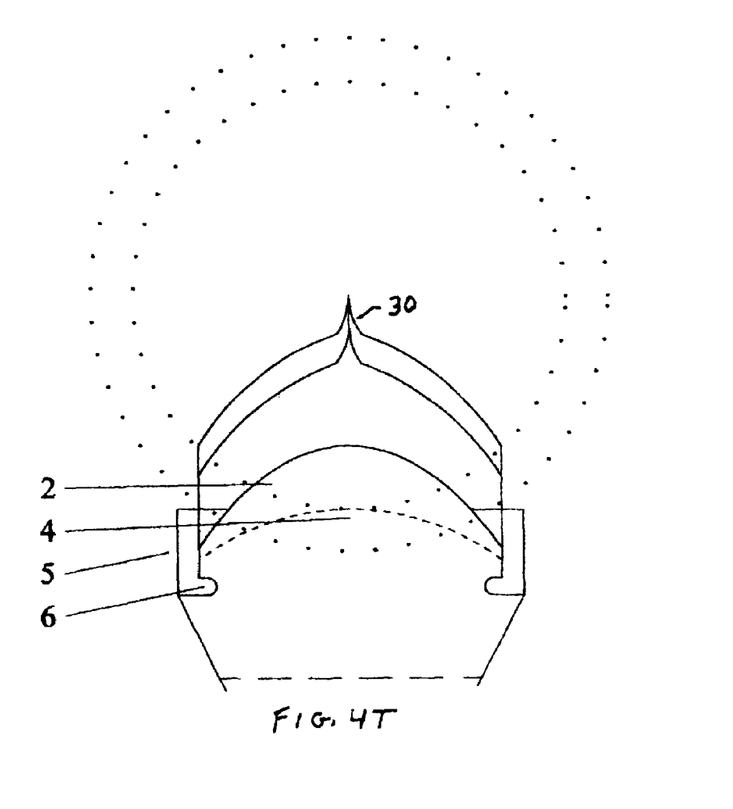
Figure 5F:
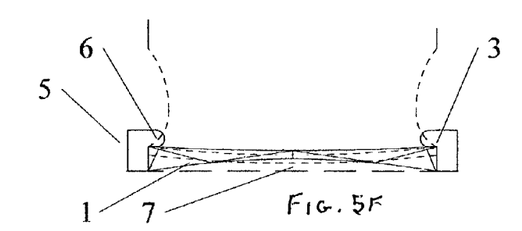
FIG. 5 is also a wedged keratome 7.0 mm wide but with two narrower blades. This blade is arched to slice more through the middle of the cornea's layer to create the two flaps more evenly for better sealing.
Figure 5S:
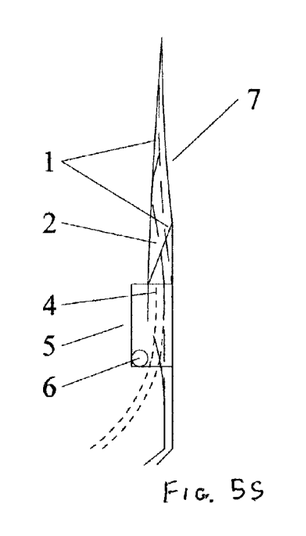
Figure 5T:
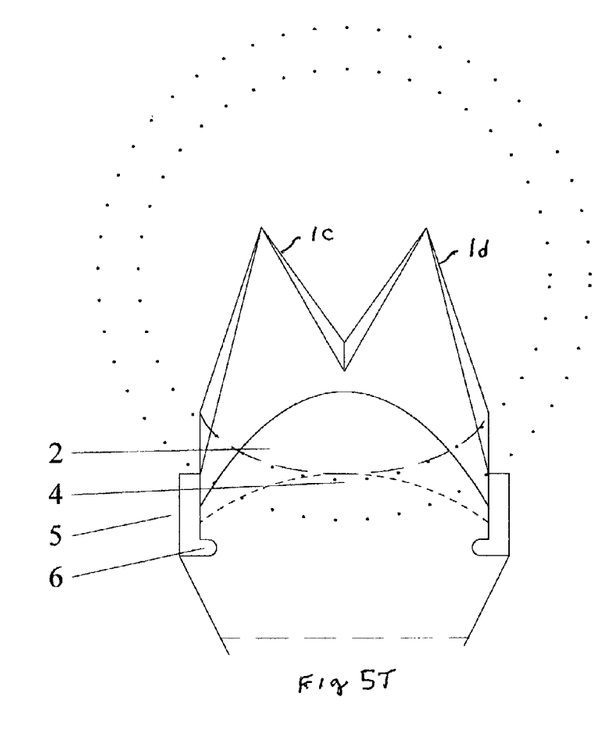
Figure 6F:
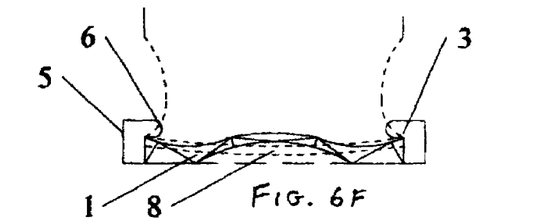
FIG. 6 is a wedged keratome 4.0 mm wide with three blades, even narrower, forming an arch like an apple coring knife, as seen in the front and side views. This figure along with FIG. 5, discloses blades with novel multiple blade tips that create a wide incision by simultaneously making a set of several small incisions that are connected together in one stroke.
Figure 6S:
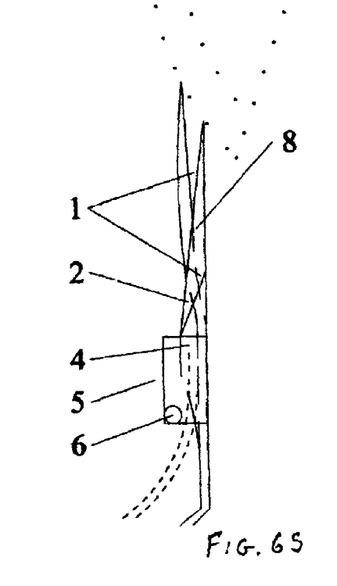
Figure 6T:
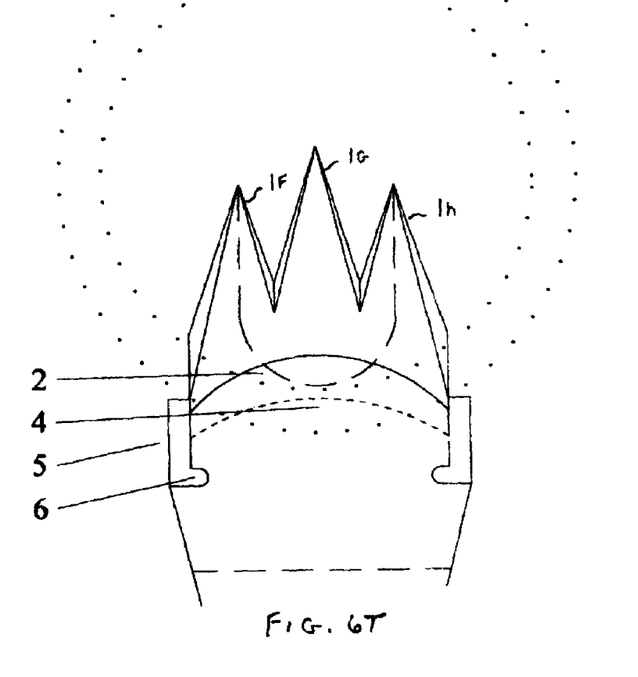

FIGS. 4 through 6 (front and side views) show each of the three available types of blades of the keratome-forming wedges, first as the blade is inserted to allow simultaneous insertion of the lens glide (fine dashed lines), and then the blade is removed while allowing the tip of the lens glide 4 to remain inside the eye for insertion of the remainder of the lens glide 10. FIGS. 4 through 6 also show how the shape of the blade 3, with the sides higher than the center and front, enables the blade to lift open the incision, while aiding the curved tip of the lens glide 4 to slip into the eye. The keratomes have two sidewalls 5 that hold the lens glide in position. These sidewalls also serve to safely stop the blade from advancing too far, placing the tip of the lens glide within the incision, and serving to control the eye by restricting its movement as the lens glide is momentarily pushed further into the anterior chamber another 2 mm. FIGS. 4 through 6 also depict pins 6 from the sidewalls that may be necessary to keep the tip of the lens glide 4 down against the keratome blade during the incision.

FIG. 4 shows a keratome with a single-point blade that is 7.0 mm wide but less tapered than most keratomes to produce a single, but wider flap. A peaked tip assists in making the IOL incision from this less-tapered blade, and the tip of this blade may optionally be used to make side-port incisions. FIGS. 5 and 6 show 7.0 mm (2-point) and 6.0 mm (3-point) keratomes, respectively, with multiple blade tips to create multiple corneal flaps, essential for creating self-sealing incisions. FIG. 5 shows the keratome blade to be slightly arched 7 to approximate the corneal curvature at the location of the intended incision to make a more uniform flap with a wider keratome. FIG. 6 shows the keratome blade more steeply arched 8 to produce a "frown" incision that is known to induce less astigmatism.

Figure 12F:
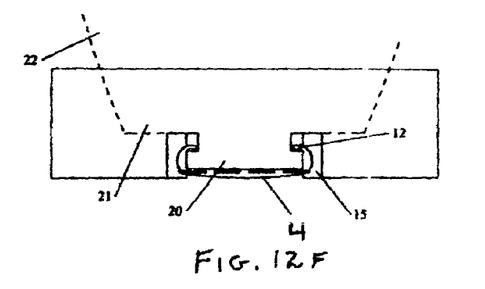
FIG. 12 show the IOL Injector consisting of a lens glide member that wedges into the incision, and an inserter that slides the IOL into the eye.

As shown in FIG. 12, the tip 4 of the lens glide 10 is clear, flexible and rounded in front, but it may optionally have elongated notches on both sides 9 to clear the pins 6 on the keratome's sidewalls 5 (FIG. 4-F,) when the keratome is removed. The remainder of the IOL Injector is made by an injection-molding type process from a rigid, inert, polymer-like substance that resists deformation or bowing when wedged into the eye.

FIG. 12 shows the IOL Injector with its two components, the lens glide 10 and the inserter 20.

Figure 12S:
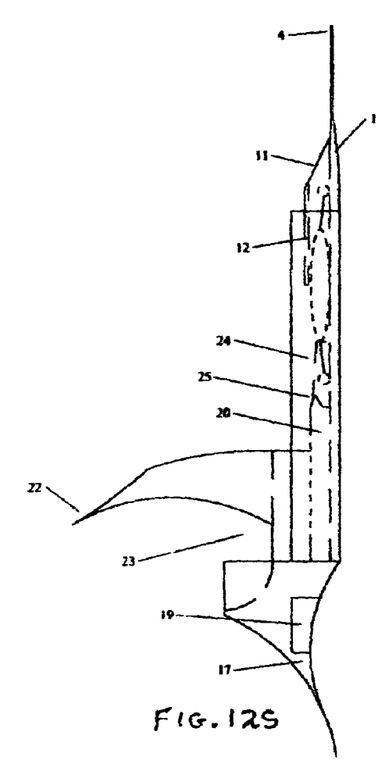
Figure 12T:
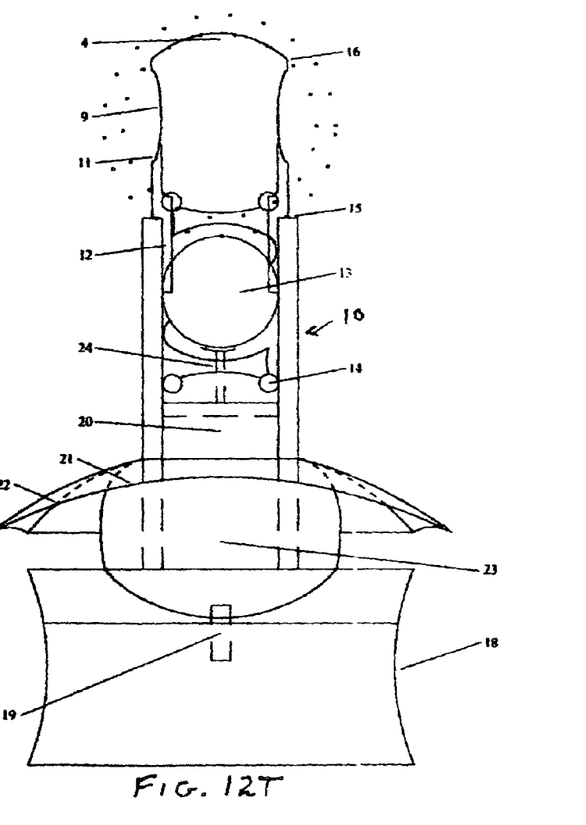
Figure 15:
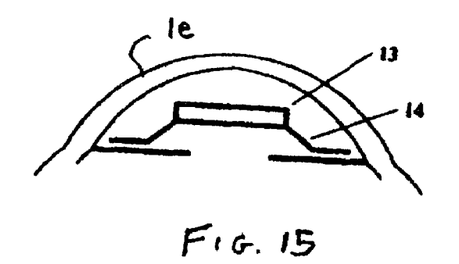
FIG. 15 illustrates the raised positioning of the lens optic relative to its haptic.

The posterior side of the lens glide 10 is boat-shaped (FIG. 12-S) to efficiently wedge open the incision and to provide structural support and room for the IOL. The two sides of the lens glide elevate like a ramp, forming two sidewalls 11 to wedge open the incision and to guide the insertion of the IOL. These sidewalls curve into an overhanging ledge 12 to move the corneal flap out of the path for the IOL insertion. This ledge 12 also keeps the IOL in a position of minimum cross-sectional area for insertion, because the optic of these IOLs 13 is typically vaulted up (anterior) about 1 mm from its haptics 14 (FIG. 15). These two sidewalls 11 extend slightly to both side stop portions 15 to stop the lens glide when it is fully inserted into the eye 16 and to control the eye. This feature serves to restrict the movement of the patient's eye in any direction except away from the Injector. These two sidewalls 11 also serve as a rail upon which the inserter 20 or plunger slides. The channel to the lens glide is just long enough to contain the IOL and the inserter.

Figure 13:
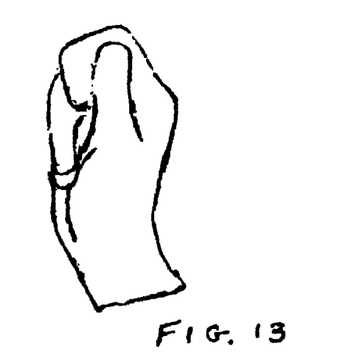
FIGS. 13 and 14 illustrate hand positioning of the surgeon while performing the method of the invention.
Figure 14:
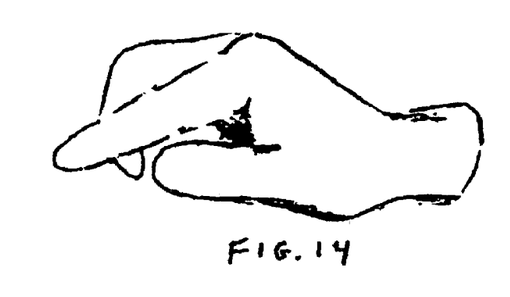

The lens glide can be held comfortably in either of two ways: by holding the trailing-edge handle 17 (FIG. 12-S) on the top and bottom with the thumb and index finger of the primary hand in a palm-up (supine) position (FIG. 13); or, alternatively, by holding the handle at the sides 18 (FIG. 12-T) with the thumb and middle finger and with the index finger resting on top in a palm-down (pronated) position (FIG. 14). This handle also has a narrow slot 19 about 3 mm long, 1 mm wide and 2 mm deep to fit onto a 2 mm pin 28 located on top of the keratome handle (FIG. 11). This slot and pin stabilize the lens glide on the keratome handle and allow the lens glide to slide forward the 2 mm necessary to wedge it into the incision and to keep it in place while the keratome is removed.

The inserter 20 in FIG. 12 has a base 20 that slides in the channel of the lens glide to push the IOL via haptics 14, and wings 21 that slide on the sidewalls for stability. The wings extend on top (anterior) to form a sail 22 that serves (a) as a handle for the left or right (secondary) hand for two-handed operation, and (b) as a pocket 23 for the primary hand's index finger during one-handed operation, allowing the other (secondary) hand to stabilize the eye. Because this design eliminates the cornea as a source of resistance during insertion, the inserter pushes the IOL by the haptics 14 into the eye, but an arm 24 may be added to also push on the optic 15 if necessary. As shown in FIG. 12-S, the tip 25 of the inserter is beveled slightly downward (posterior) on top to assist entry under the ledge 12, and is then angled more sharply back and down (posterior) like the bow of a ship to keep the IOL haptic down (posterior), particularly as the lens glide is removed.

Surgical Procedure

1. Preoperatively, the surgeon inspects all components and assembles the IOL Injection System as follows:
   a. Deposits a small amount of viscoelastic fluid into the channel of the lens glide for lubrication, then inserts the IOL into its position in the channel.
   b. Slides the IOL forward so the edges of the optic 13 are beneath the ledge 12 as shown in FIG. 2-S.
   c. Places the inserter 20 into the channel.
   d. Mounts the IOL Injector on the selected keratome (1-, 2- or 3-point blade) by placing (a) the tip 4 of the lens glide 10 on the face of the keratome blade 2 and under the pins 6, see FIG. 4-S and (b) the pin 28 on the keratome's handle into the front part of the notch 19 in the lens glide handle.
2. If desired, the surgeon uses the tip 30 of the keratome blade to make a small (1 mm) side-port incision. The surgeon or assistant then inflates the eye by injecting a viscoelastic fluid through this incision in standard fashion.
3. Beginning near the base of the cornea (limbus), the surgeon holds the keratome in the primary hand to make a Z-type, multiplanar (Langerman) self-sealing incision into the clear cornea. The correct depth of the incision is indicated when resistance is felt as the keratome's stop 5 contacts the cornea as shown in FIG. 4-S.
4. The index finger of the surgeon's primary hand pushes the IOL Injector handle forward about 2 mm until it stops. This motion of the IOL Injector wedges the tip of the lens glide into the incision, which allows the lens glide to remain in position in the eye as the keratome is removed.
5. The surgeon's secondary hand (or an assistant) lifts and holds the handle of the IOL Injector away from the keratome handle, while the surgeon's primary hand removes the keratome.
6. The surgeon transfers the IOL Injector to the primary hand, and inserts the lens glide into the eye until resistance is felt as the stop 15, shown in FIG. 12-T, contacts the cornea.
7. The surgeon inserts the IOL, operating the IOL Injector using one of two methods:

a. Two-handed, with the device held palm up (hand supine); the thumb and index finger of the primary hand hold the Injector, allowing the secondary hand to slide the inserter (FIG. 13).
b. One-handed, palm down (hand pronated); the thumb and middle finger hold the sides of the handle, while the index finger rests on top to slide the inserter 20 (FIG. 14).

8. The primary hand then withdraws the lens glide from the cornea, thus allowing the IOL to slip down (posterior) into position at the angle of the anterior chamber.
9. The surgeon removes the inserter. It may be necessary to tilt the inserter while withdrawing it, to release the IOL completely.
10. The surgeon or assistant irrigates the anterior chamber through the side-port incision to remove any remaining viscoelastic fluid by means of the IOL incision.
11. The surgeon then checks the IOL incision for leaks.

There is a notable option to this design and procedure. A Fliering a (stabilizing) Ring or bridal suture placed below (posterior to) the IOL incision may provide additional safety, control and counter-traction during insertion of the lens glide.

Preferred Knives

The preferred keratome knife has blades that are significantly different from the patents listed above.

Figure 3:
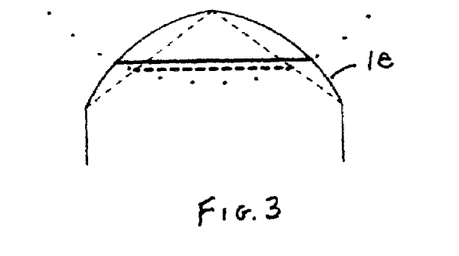
FIGS. 3 and 7-10 illustrate various aspects of the novel knives of the invention.
Figure 7:
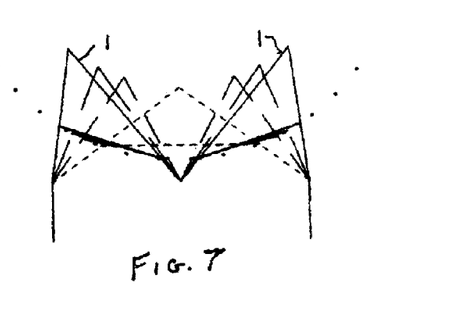
Figure 8:
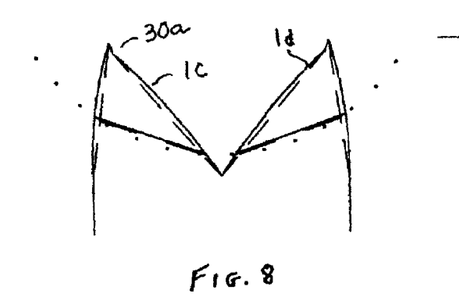
Figure 9:
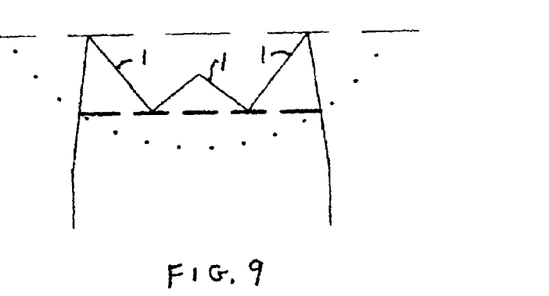
Figure 10:
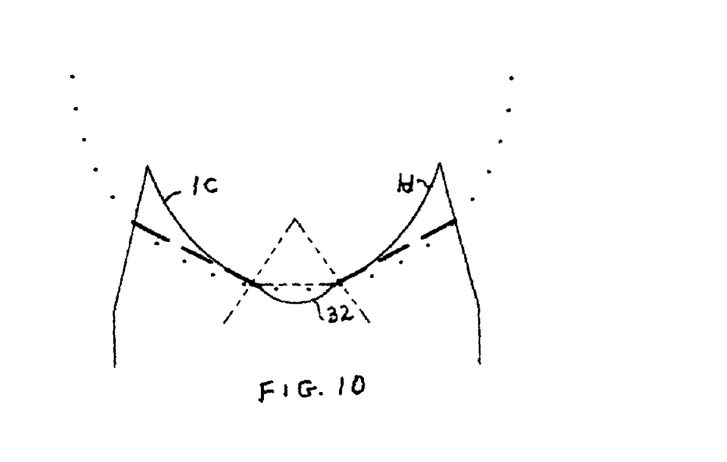

(1) For the same depth of the Z-shaped, multi-planar (Langerman) incision, a less tapered and more rounded blade will create a wider flap (FIGS. 3 and 4).
(2) Multiple blade tips (FIGS. 5 and 6) create a wide incision by simultaneously making a set of several small incisions that are connected together in one stroke. The fact that each blade tip has only a limited depth means the resulting wide incision can be created without the need to penetrate deeply into the cornea, as would be necessary with a single-point blade of the desired width. This is especially beneficial for creating Z-shaped incisions, which become self-sealing when internal pressure pushes the inner layer against the outer layer. The capability to make multiple such Z-shaped incisions in a single stroke is a major advance that shortens the process significantly, which in term results in less trauma to the eye and streamlines the entire procedure.
(3) In general, blade tips placed farther apart will create wider flaps and a wider incision with a more effective self-sealing mechanism (FIG. 7). This design takes advantage of incisions up to about 3 mm wide made straight and parallel to the iris plane, which generally do not leak (Fine).
(4) A sharply pointed tip (FIGS. 4 and 8) helps to make the incision easier (Gould) and may optionally permit the keratome to be used for making very small, side-port incisions that are needed to inflate the eye with a syringe (FIGS. 4-6, and 7-10).
(5) When combining (1), (2), (3) and (4) above, less tapered, more rounded and multiple blade tips spaced further apart will create even wider flaps and more effective self-sealing incisions (FIG. 8).
(6) Because two points or blade tips determine a line or axis of rotation, any additional blade tips should be on or immediately adjacent to this axis or should contribute to making the incision upon rotating the keratome for these Z-shaped incisions (FIG. 6). Otherwise, the keratome will act similar to a bottle-opener and will contort the cornea (FIG. 9). For this and other reasons, 10-mm wide keratomes for Planned Extracapsular Cataract Extraction (P-ECCE) have dual tips to create two large, self-sealing peripheral flaps by the Z-incision (FIG. 10). The center of this keratome is designed to avoid cutting the cornea in the same location where a central 3-mm incision was made previously to prepare the cataract for removal. One or more sutures or retaining devices like staples placed within the central 3 mm incision may be necessary for safety. The inner cutting edge is curved backward to create a sharper, more pointed blade and to require less effort in making the incision by a slicing effect (Lager, U.S. Pat. No. 5,217,477). Because the blade is less tapered toward the center, the blade may require a series of slight rotations to complete the incision by slicing.

(7) Curved blades:
a. Slightly curved (FIG. 5-F) blades create corneal flaps that are larger and of more uniform thickness to permit better sealing, particularly for single-pointed blades, because the corneal curvature is now significant for these wider blades, or
b. More steeply curved (FIG. 6-F) blades, shaped like apple coring knives, create "frown"-shaped incisions. These curved blades for curved incisions (Muller-Jensen) are known to induce less astigmatism, or less blurry vision, while effectively creating smaller incisions that may stretch open wider (McGowan).

Thus the keratome knifes of the invention are configured to cut one or more self-sealing corneal flaps in a single surgical stroke, and have at least one wedge-shaped blade tip and an arched upper surface. Looking down on FIGS. 4T, 5T and 6T, the arched upper surface of the knives facing the viewer slope downwardly away from the viewer to the left and right from the central axes extending through tip 30 of FIG. 4T, blade tip 1g of FIG. 6T and the crotch between the blade tips 1c and 1d of FIG. 5T.

Wide, limited-depth surgical knives with multiple tip blades may also be used to create large, self-sealing incisions such as those needed for Extracapsular Cataract Extraction (ECCE, where a dense-cataract is squeezed out), either as a planned procedure or during (anticipated) conversion from phacoemulsification (by machine).

Injectors of similar design may place various types of (nonfoldable) IOLs into the eye, either in front of or behind the iris (anterior or posterior chamber).

REFERENCES

McGowan, Bernard L., M.D., NY IOL Implant Society meeting, May 2, 2002, New York, N.Y. Shelton, Philip, M.D., Six mm Self-Sealing Incision for Cataract Extraction and IOL implant performed Mar. 25, 2002, Anguilla, BWI.

PUBLICATIONS OF INTEREST

Fine, I H. Clear Corneal Incisions. International Opthalmology Clinics. 1994:34(2):59-72.
Galin, Gould, et al. Angle-supported Phakic Anterior Chamber Lenses. Operative Techniques in Cataract and Refractive Surgery, March 2000, 43-8.
Gould, Herbert L., M.D. Chapter 9: Phakic 6H Angle-Supported Phakic IOLs, in Refractive Surgery with Phakic IOLs, by Jorge L. Alio and Juan J. Perez-Santonja, M.D.s, 2002.

Jaffe, Norman S., M.D. Cataract Surgery and Its Complications. Mosby, St. Louis, 1997, pp. 29-31, 74-76.

Koch, Paul S., M.D. Converting to Phacoemulsification. Slack Inc., Thorofare, N.J., 1992, pp 3-29.

Langerman, D W. Architectural Design of a Self-Sealing Corneal Tunnel, Single-Hinge Incision. Journal of Cataract and Refractive Surgery. 1994; 20:84-88.

Muller-Jensen, K, et al. Stability of Astigmatism over Three Years after Corneal Stretch Incision. Journal of Refractive Surgery. 1998, 14:455-459.

Ophthalmic Innovations International at www.oii-iol.com. Surgical Guidelines for the Phakic 6 Lens, Recommended Operative Procedure.

Since modifications of the aforesaid steps and apparatus may occur to the worker in the art, the scope and spirit of the invention is to be limited solely to the terms of the following claims and art recognized equivalents thereof.

What is claimed is:

1. A keratome knife for use by a surgeon to cut into a cornea of an eyeball of a living being, said keratome knife consisting of two or three wedge-shaped sharply pointed blade tips rigidly affixed to one another for simultaneously making small incisions that are connected together in one surgical stroke, each wedge-shaped blade tip having a pair of non-serrated blade edges configured to make self-sealing corneal incisions.

2. The keratome knife of claim 1 wherein said keratome knife has an arched upper surface curved downwardly to the left and right from a central portion of said keratome knife and toward a central portion of said eyeball during incision by said surgeon.

3. The keratome knife of claim 2 wherein said arched upper surface is arched to approximate a corneal curvature of said eyeball being operated upon.

4. The keratome knife of claim 2 wherein said arched upper surface is steeply arched to produce a frown incision that has a minimal astigmatic effect.

5. The keratome knife of claim 2 wherein said keratome knife has a width of at least seven millimeters.

6. The keratome knife of claim 1 wherein said keratome knife has a width of at least seven millimeters.

7. The keratome knife of 1 wherein a scooped out valley portion is formed within a heel portion of said keratome knife, enabling a lens glide member to be inserted into a patients eye along with said keratome knife.

8. The keratome knife of claim 7 wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

9. The keratome knife of claim 1 wherein a pair of sidewalls are affixed to side portions of said keratorne knife, configured to serve as a channel on a face of said keratome knife to accommodate a lens glide member and to additionally serve as a blunt safety stop to deter the knife from entering too deeply into the eye.

10. A keratome knife for use by a surgeon to cut into a cornea of an eyeball of a living being, said keratome knife consisting of two wedge-shaped sharply pointed blade tips rigidly affixed to one another for simultaneously making small incisions that are connected together in one surgical stroke, each wedge-shaped blade tip having a pair of non-serrated blade edges meeting at a frontal keratome knife portion and configured to make self-sealing corneal incisions.

11. The keratome knife of claim 10 wherein said keratome knife has an arched upper surface curved downwardly to the left and right from a central portion of said keratome knife and toward a central portion of said eyeball during incision by said surgeon.

12. The keratome knife of claim 11 wherein said arched upper surface is arched to approximate a corneal curvature of said eyeball being operated upon.

13. The keratome knife of claim 11 wherein said arched upper surface is steeply arched to produce a frown incision that has a minimal astigmatic effect.

14. The keratome knife of claim 11 wherein said keratome knife has a width of at least seven millimeters.

15. The keratome knife of claim 10 wherein said keratome knife has a width of at least seven millimeters.

16. The keratome knife of 10 wherein a scooped out valley portion is formed within a heel portion of said keratome knife, enabling a lens glide member to be inserted into a patients eye along with said keratome knife.

17. The keratome knife of claim 16 wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

18. The keratome knife of claim 10 wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

19. A keratome knife for use by a surgeon to cut into a cornea of an eyeball of a living being, said keratome knife consisting of two or three wedge-shaped sharply pointed blade tips rigidly affixed to one another for simultaneously making small self-sealing incisions that are connected together in one surgical stroke, each wedge-shaped sharply pointed blade tip having a pair of non-serrated blade edges meeting at a frontal keratome knife portion and configured to make self-sealing corneal self-sealing incisions and wherein each wedge-shaped sharply pointed blade tip points anteriorly and has said pair of blade edges diverging from a distal forward end of said keratome knife.

20. The keratome knife of claim 19 wherein said keratome knife has an arched upper surface curved downwardly to the left and right from a central portion of said keratome knife and toward a central portion of said eyeball during incision by said surgeon.

21. The keratome knife of claim 20 wherein said arched upper surface is arched to approximate a corneal curvature of said eyeball being operated upon.

22. The keratome knife of claim 20 wherein said arched upper surface is steeply arched to produce a frown incision that has a minimal astigmatic effect.

23. The keratome knife of claim 20 wherein said keratome knife has a width of at least seven millimeters.

24. The keratome knife of claim 19 wherein said keratome knife has a width of at least seven millimeters.

25. The keratome knife of 19 wherein a scooped out valley portion is formed within a heel portion of said keratome knife, enabling a lens glide member to be inserted into a patients eye along with said keratome knife.

26. The keratome knife of claim 25 wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

27. The keratome knife of claim 19 wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

28. A keratome knife for use by a surgeon to cut into a cornea of an eyeball of a living being:
   (a) wherein said keratome knife having multiple wedge-shaped sharply pointed blade tips rigidly affixed to one another for simultaneously making small incisions that are connected together in one surgical stroke, each wedge-shaped sharply pointed blade tip having a pair of non-serrated blade edges meeting at a frontal keratome knife portion and configured to make self-sealing corneal incisions and wherein each wedge-shaped sharply pointed blade tip points anteriorly and has said pair of blade edges diverging from a distal forward end of said keratome knife; and
   (b) wherein said keratome knife has an arched upper surface curved downwardly to the left and right from a central portion of said keratome knife and toward a central portion of said eyeball during incision by said surgeon;
   (c) wherein a scooped out valley portion is formed within a heel portion of said keratome knife, enabling a lens glide member to be inserted into said eyeball along with said keratome knife, and
   (d) wherein a pair of sidewalls are affixed to side portions of said keratome knife, configured to serve as a channel on a face of said keratome knife to accommodate a lens glide member and to additionally serve as a blunt safety stop to deter the knife from entering too deeply into the eye.

29. The keratome knife of claim 28 wherein said keratome knife has a width of at least seven millimeters.

* * * * *